(12) United States Patent
Banks

(10) Patent No.: US 6,670,617 B2
(45) Date of Patent: Dec. 30, 2003

(54) MIRROR FLUOROMETER

(75) Inventor: Rodney H. Banks, Aurora, IL (US)

(73) Assignee: Ondeo Nalco Company, Naperville, IL (US)

( * ) Notice: Subject to any disclaimer, the term of this patent is extended or adjusted under 35 U.S.C. 154(b) by 84 days.

(21) Appl. No.: 09/893,831

(22) Filed: Jun. 28, 2001

(65) Prior Publication Data

US 2003/0006385 A1 Jan. 9, 2003

(51) Int. Cl.[7] .................................................. G01J 1/58
(52) U.S. Cl. .................................. 250/458.1; 250/459.1
(58) Field of Search .......................... 250/458.1, 459.1, 250/461.1; 356/317, 318

(56) References Cited

U.S. PATENT DOCUMENTS

| | | | |
|---|---|---|---|
| 4,783,314 A | | 11/1988 | Hoots et al. |
| 5,221,958 A | * | 6/1993 | Bohnenkamp ............. 356/318 |
| RE34,782 E | * | 11/1994 | Dandliker et al. ........ 250/458.1 |
| 5,955,736 A | * | 9/1999 | Robinson et al. ........ 250/458.1 |
| 6,060,318 A | | 5/2000 | Moeggenborg et al. |
| 6,317,207 B2 | * | 11/2001 | French et al. ................ 356/317 |
| 6,369,894 B1 | * | 4/2002 | Rasimas et al. ............. 356/417 |
| 2002/0192808 A1 | * | 12/2002 | Gambini et al. ......... 435/287.2 |

* cited by examiner

Primary Examiner—David Porta
Assistant Examiner—Christine Sung
(74) Attorney, Agent, or Firm—Margaret M. Brumm; Thomas M. Breininger

(57) ABSTRACT

Described and claimed is a Mirror Fluorometer comprising a rotatable mirror positioned such that it is capable of projecting a converging cone of excitation light onto one or more of the samples wherein the fluorescent signals emitted from fluorophores in the samples is detected. Also claimed is a method of using this Mirror Fluorometer for detecting fluorescent signals emitted by one or more fluorophores from samples from a natural or industrial water system. The fluorometer, when coupled with a controller is capable of monitoring and optionally controlling an industrial process or system, including a paper mill process.

15 Claims, 3 Drawing Sheets

MIRROR FLUOROMETER

FIELD OF THE INVENTION

The present invention relates generally to analytical devices and methods for monitoring and optionally controlling natural or industrial processes or systems. More specifically, the present invention relates to a fluorometer capable of detecting fluorescent signals emitted by one or more fluorophores present in samples from natural or industrial processes or systems. By using this fluorometer it is possible to monitor and optionally control the process or system.

BACKGROUND OF THE INVENTION

A fluorometer is an analytical device that typically contains a light source, a means of selecting the desired excitation wavelength range, a sample cell, a means of selecting the desired emission wavelength range and a detector.

A spectrofluorometer is a specific type of fluorometer where the means for selecting the excitation and/or emission wavelength range is performed by a grating. A grating acts to disperse a continuum of light into its components. Spectrofluorometers may be further subdivided into scanning spectrofluorometers, which are those that use a mechanical means to scan the wavelength spectrum based on the position of the grating relative to the excitation source and/or emission (this describes a standard laboratory model fluorometer), or fixed spectrofluorometers where the grating is fixed with respect the emission. The emission (fluorescence) is then directed to an array of detectors. The array of detectors could be charge coupled devices, usually abbreviated "CCD" or the array of detectors could be photodiodes. The detectors are then calibrated in the appropriate wavelength units. A commercial device such as this is available from Drysdale and Associates, Inc., P.O. Box 44055, Cincinnati, Ohio 45244 (513) 831-9625. This type of fixed spectrofluorometer still requires the appropriate excitation wavelength selection device, which could be a scanning, grating or filter.

The fluorometers that are most suitable for use under field conditions are not grating spectrofluorometers, rather, they are filter-based fluorometers. A filter-based fluorometer uses a filter to exclude all but the selected wavelength range. In general, currently available and known filter-based fluorometers have one channel with this channel containing an optically appropriate cell.

A light source and an optional excitation filter, are positioned on one side of the optically appropriate cell, and an emission detector and an emission filter are positioned on the opposite side of the optically appropriate cell. A reference detector may optionally be present. Because fluorescence is isotropic, most fluorometers detect any fluorescent light emitted from the fluorophore at a 90° angle from the light source in order to minimize collection of any spurious excitation light.

The excitation filter permits light of the chosen excitation wavelength range to pass through the filter and into the cell. When conducting off-line batch testing, a sample of, for example, water from a natural or an industrial water system is placed and held in the optically appropriate cell. When conducting on-line testing the sample of water can flow through the optically appropriate cell. The light is absorbed by a fluorophore present in the water sample, which, in turn, emits a fluorescent light (hereinafter known as a fluorescent signal) having the same or a longer wavelength than the excitation light. The emission filter, which is positioned between the emission detector and the optically appropriate cell, is chosen so as to permit only the light emitted by the fluorophore (the fluorescent signal of the fluorophore) to pass through the filter to the emission detector.

One of the known uses of fluorophores in industrial water systems or in hydrology in general is the use of inert fluorescent tracers for determining the hydraulic losses in an industrial water system. Furthermore, using fluorescent tracers for controlling additive or product dosage to a recirculating or once-through cooling water system is also known (see U.S. Pat. No. 4,783,314). In this method, a fluorescent tracer is combined with one or more additives in a known proportion of tracer to additive(s) and then the mixture is added to the water of a cooling system. A fluorometer is then used to detect the presence and concentration of the fluorescent tracer in the cooling water and therefore the presence and concentration of the amount of additive. A limitation of currently available fluorometers is that, in general, they have only one channel that contains an optical cell for measuring fluorescence in a single process sample (i.e., a one-channel-sample fluorometer). Another limitation of currently available fluorometers is that the majority of known fluorometers are not suitable for measuring fluorescent signal(s) in opaque mediums, such as opaque slurries, opaque colloids and certain opaque Metal Working Fluids.

There exists a need for an fluorometer which is capable of monitoring several process samples using a single apparatus without having to replace a process sample, and the need for fluorometers capable of measuring fluorescent signals in an opaque medium.

SUMMARY OF THE INVENTION

The first aspect of the instant claimed invention is a fluorometer comprising:
an excitation light source for generating a collimated beam of excitation light;
a rotatable mirror positioned such that it is capable of accepting a collimated beam of light from said excitation light source and projecting a converging cone of excitation light onto one or more samples;
a sample holder comprising one or more channels, wherein each channel is capable of holding an optical cell containing a sample; and
a detector capable of detecting the fluorescent signals from fluorophores presents in said one or more samples.

The second aspect of the instant claimed invention is a fluorometer comprising:
an excitation light source for generating a collimated beam of excitation light;
a rotatable mirror positioned such that it is capable of accepting a collimated beam of light from said excitation light source and projecting a converging cone of excitation light onto one or more samples;
a sample holder comprising one or more channels, wherein each channel is capable of accepting an optical cell containing a sample;
a detector capable of detecting the fluorescent signals from fluorophores presents in said one or more samples; and
a controller that uses the fluorescent signals detected by said fluorometer for monitoring and/or control of the natural or industrial process from which the samples are taken.

The third aspect of the instant claimed invention is a method of fluorometrically detecting fluorophores present in one or more samples, the method comprising the steps of:
a) providing a fluorometer, wherein said fluorometer is described in the first aspect or in the second aspect of the instant claimed invention;

b) providing one or more samples from a natural or industrial process stream; and c) using said fluorometer to detect the fluorescent signals of said fluorophores in said samples.

DETAILED DESCRIPTION OF THE INVENTION

Figure 1:
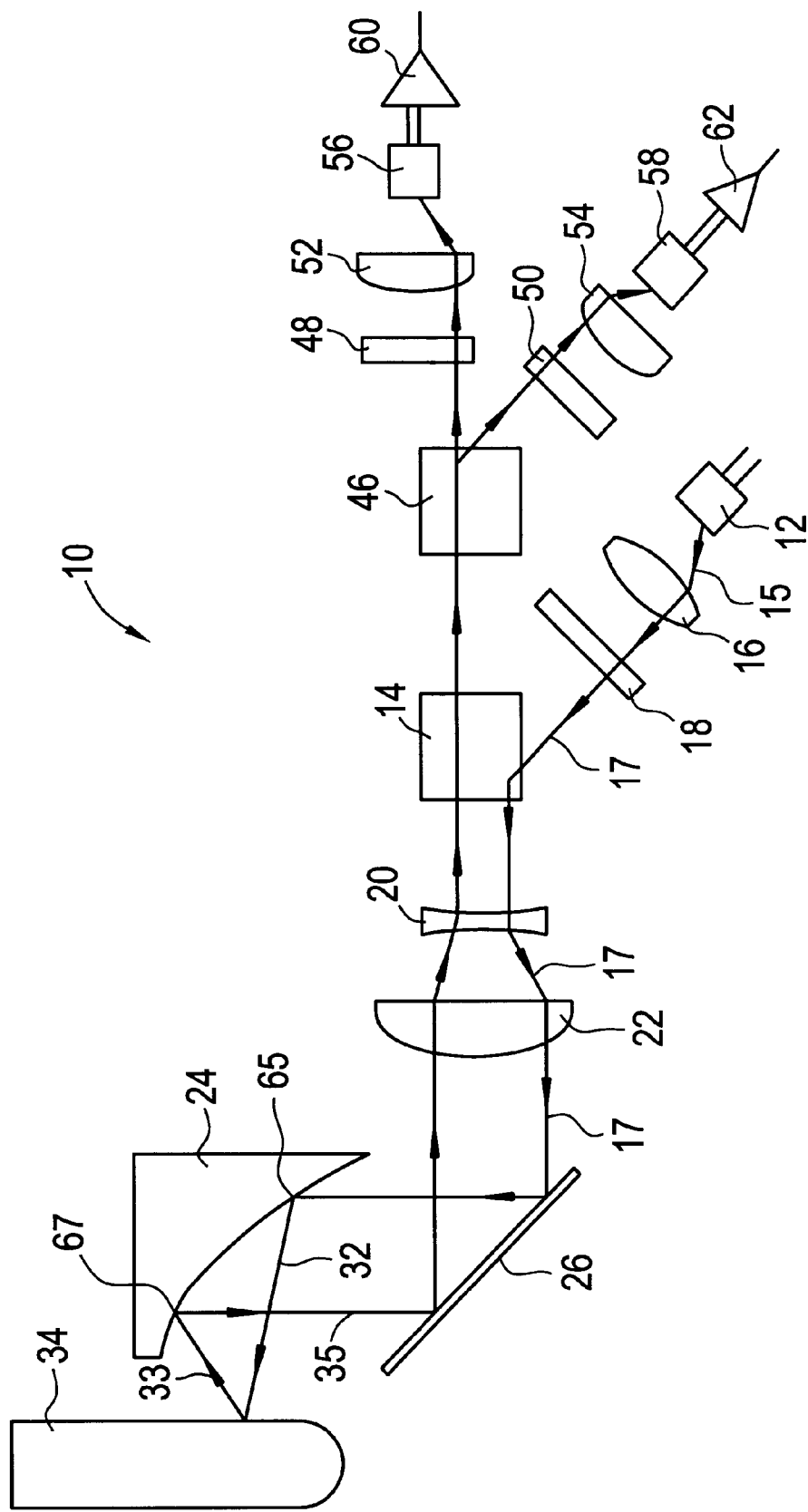
FIG. 1 is a side perspective view of a fluorometer capable of measuring the fluorescent signals in a single sample made in accordance with the present invention.

Throughout this patent application the following words have the indicated meanings:

"beam" means a cylindrical projection of multiple rays of light.

"collimated" means light rays that are mutually parallel.

"cone" means a projection of multiple rays of light to one focal point.

"converging" means light rays that "come to" or are "directed to" to the same focal point.

"diverging" means light rays that originate from one point and that are not directed to the same focal point and do not travel in parallel lines.

"fan" means a projection of multiple rays of light from a point source to an angle up to 180°.

A "fluorophore" is a molecule that, upon absorption of a photon of energy (hv) that results in an electron being promoted from the molecular electronic ground state ($S_0$) to an electronic excited state ($S_1$ or $S_2$ or $S_3$) and subsequently relaxing to the lowest vibronic state of excited state $S_1$, emits a photon of energy "E" (hv) that is lower in energy (though longer in wavelength) than was absorbed. Note that this relationship can be illustrated with the equation: $E_{(absorption)} > E_{(fluorescence)}$. This emission of energy results in the molecular electronic state being returned to the ground state ($S_0$). The overall process results in emission of fluorescent photons in an isotropic distribution. The fluorophores capable of being detected by the instant claimed fluorometer must be capable of absorbing excitation light in the wavelengths of from about 200 nm to about 1200 nm and emitting it at a longer wavelength than the excitation light.

"Inert" refers to the fact that an inert fluorophore is not appreciably or significantly affected by any other chemistry in the natural or industrial process, or by the other system parameters such as metallurgical composition, microbiological activity, biocide concentration, heat changes or overall heat content. To quantify what is meant by "not appreciably or significantly affected", this statement means that an inert fluorophore has no more than a 10% change in its fluorescent signal, under conditions normally encountered in the natural or industrial process. Conditions normally encountered in natural or industrial processes are known to people of ordinary skill in the art of natural or industrial processes.

"Isotropic" refers to the fact that if a moiety is considered a point source, and excitation light is directed at the moiety, fluorescent light is emitted equally over $2\pi$ steradians, creating, in effect, a sphere in 3 dimensions. Because of the isotropic distribution of fluorescent light, in practice, collection of the fluorescent light signal can occur, for example, at 90° relative to the excitation (photon) source to minimize the photons (light) collected that are attributed to the excitation (photon) source. This also helps to minimize light scattering.

"Nalco" refers to ONDEO Nalco Company, ONDEO Nalco Center, 1601 W. Diehl Road, Naperville, Ill., (630) 305-1000.

"nm" means nanometers; which are $10^{-9}$ meters.

The present invention provides a fluorometer that is capable of monitoring, detecting or measuring fluorescent light emitted from fluorophores present in one or more samples. The fluorometer which includes a rotatable mirror that is positioned such that the rotatable mirror accepts a collimated beam from the light source and then the rotatable mirror projects a converging or focused beam of excitation light onto each of the samples in sequence or in a stepped manner. The emitted converging cone of excitation light from the fluorophores present then is accepted by the rotatable mirror which projects a collimated beam of excitation light on through to a detector which detects the fluorescent signal at the selected wavelength of whatever fluorophore is present in the sample. The fluorescent signals subsequently detected can be further processed such that the fluorometer can be used to monitor and optionally control a process or system.

It has been discovered that the rotatable mirror can facilitate the use and operation of the fluorometer, particularly where multiple samples are required to be fluorometrically monitored during a given test period. The fluorometer of the present invention includes a sample holder that can be configured to hold one or more of the samples to be tested during a given test period. Once the samples are loaded into the sample holder, each sample can then be separately or individually tested or analyzed by rotating the mirror to move and project the converging beam from one sample to the next until all of, or a portion of, the samples within the sample holder have been tested.

Figure 2:
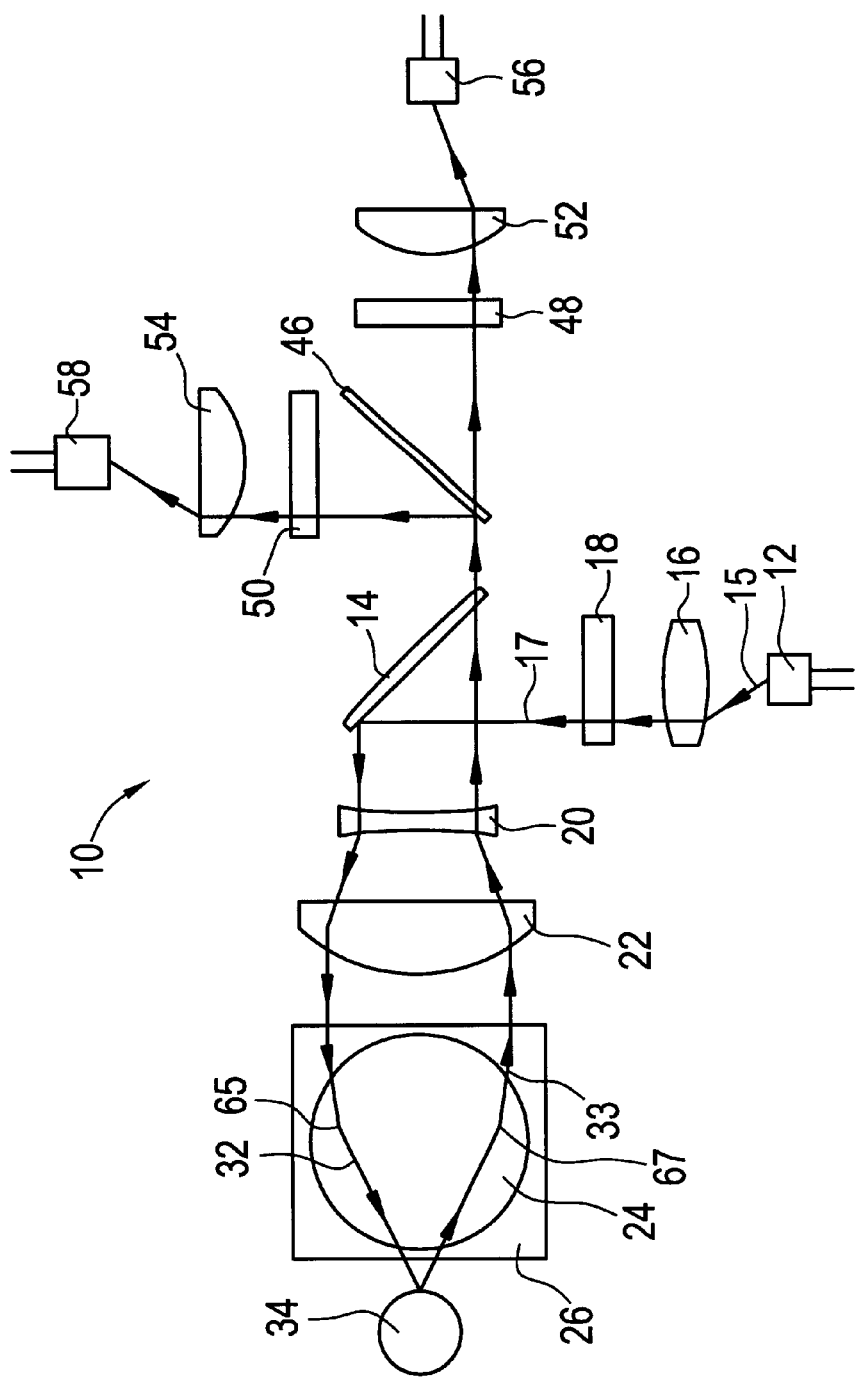
FIG. 2 is a top perspective view of a fluorometer capable of measuring the fluorescent signals in a single sample made in accordance with the present invention.

In FIG. 1 and in FIG. 2, the first aspect of the present invention is illustrated. Single-Sample Mirror Fluorometer 10 includes an excitation light source 12 that can transmit excitation light 15 through a series of filters and lenses to generate a collimated beam of excitation light 17. The filters are used to filter out or exclude all but the selected wavelength range of the excitation light. The lenses are used to focus or collimate the light to adapt to the size and dimension requirements of the fluorometer components such as the mirrors, the filters, the detectors and the like.

It should be appreciated that if the spectral range of the excitation light source is sufficiently narrow or monochromatic, or the fluorophore stokes shift is significantly large so that there is no spectral overlap between the excitation light spectrum of light source and the emission spectrum of the fluorophore, then the use of an excitation filter is optional.

Figure 3:
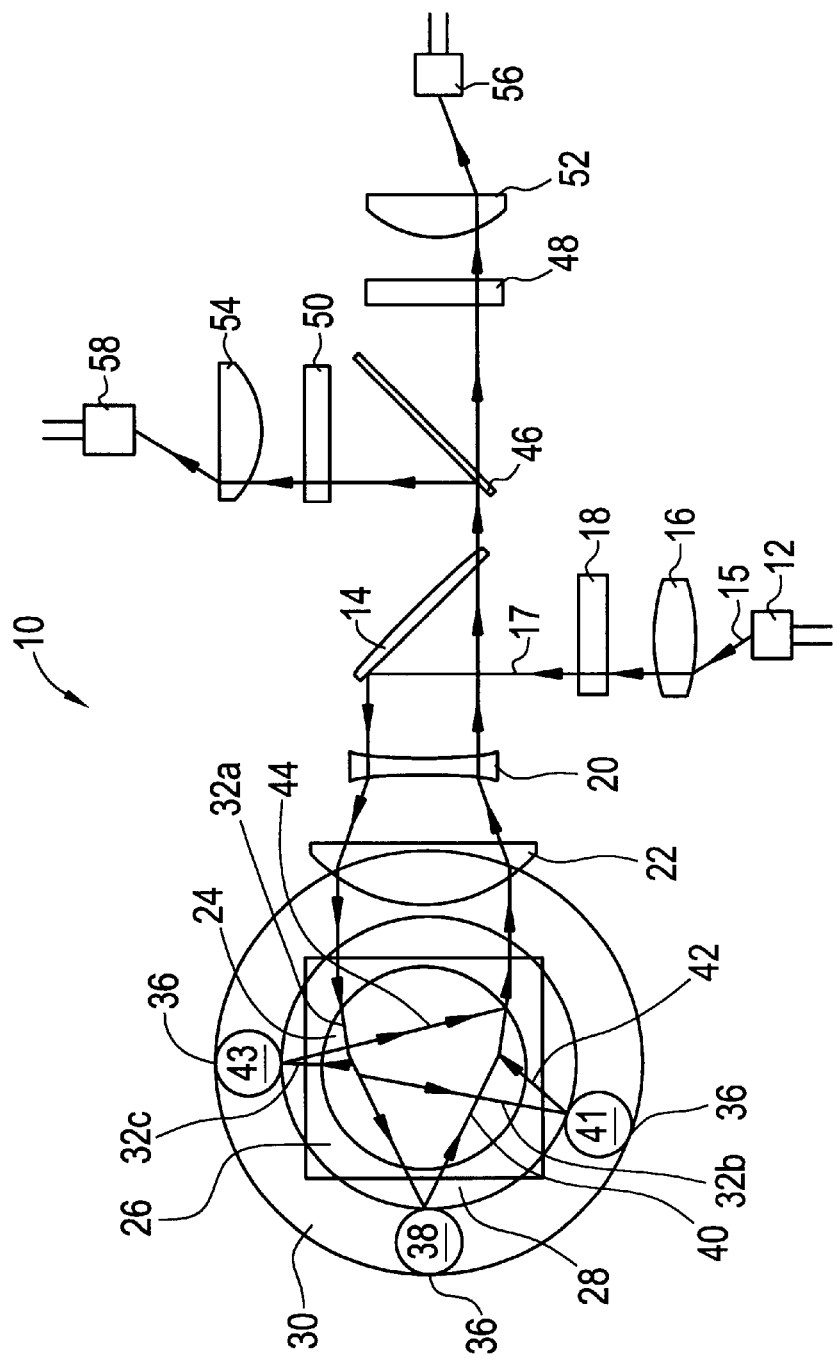
FIG. 3 is a top perspective view of a fluorometer capable of measuring the fluorescent signals in multiple samples made in accordance with the present invention.

Any number, type and configuration of excitation light sources, lenses and filters can be used to generate collimated beam of excitation light 17. In all aspects of the instant claimed invention, the excitation light source 12 transmits a beam of excitation light 15 to an excitation dichroic filter 14 through an aspheric lens 16 and an excitation filter 18 as shown in FIG. 1 and FIG. 2 and FIG. 3. Collimated beam of excitation light 17 is then further transmitted through a double concave lens 20 and a piano convex lens 22 to directional mirror 26. Directional mirror 26 directs collimated beam of excitation light 17 to rotatable mirror 24. Double concave lens 20 and piano convex lens 22 are used to adjust (adjusting in this instance meaning to increase) the size of collimated beam of excitation light 17 before it is transmitted to rotatable mirror 24.

As further illustrated in FIG. 1 and FIG. 2 and FIG. 3, directional mirror 26 is provided to direct the collimated beam of excitation light 17 to rotatable mirror 24. Directional mirror 26 can be any suitable mirror, such as a flat mirror. It should be appreciated that the need for directional mirror 26 is optional and depends on the configuration of the fluorometer. It should also be appreciated that the present invention is not limited by the size, type, shape and position of directional mirror 26 relative to rotatable mirror 24.

The collimated beam of excitation light 17 strikes rotatable mirror 24 all over. An individual intersection point 65 is shown on FIG. 1 and FIG. 2 to illustrate one point where one ray of collimated beam of excitation light 17 strikes rotatable mirror 24. Rotatable mirror 24 then projects onward a converging cone of excitation light 32 which strikes sample 34 and excites fluorophores present in said sample. The fluorophores present in sample 34 then emit fluorescent light in a diverging fan of emitted light 33. This diverging fan of emitted light 33 then leaves sample 34 and strikes rotatable mirror 24 all over. An individual intersection point 67 is shown on FIG. 1 and FIG. 2 to illustrate one point where one ray of diverging fan of emitted light 33 strikes rotatable mirror 24. Rotatable mirror 24 then projects onward a collimated beam of emitted fluorescent light 35 to directional mirror 26. Collimated beam of emitted fluorescent light 35 then travels through piano convex lens 22 and double concave lens 20 and emission dichroic filter 46.

The sample can emit fluorescent light due to the presence of one or more fluorophores within the sample. Regarding the description of the fluorophores capable of being detected by the instant claimed fluorometer, it is necessary to note that in order to be detectable by the instant claimed fluorometer, the fluorophore must be capable of absorbing light in the wavelengths of from about 200 nm to about 1200 nm and emitting it at a slightly longer wavelength. Preferably, the fluorophores absorb light in the wavelengths of from about 350 nm to about 800 nm.

Emission dichroic filter 46 acts to separate the light into emission bands. Each emission band is passed through a separate emission filter 48 or 50 and from there to a separate piano convex lens 52 or 54 and from there to separate detectors 56 or 58. Each of detector 56 or 58 generates an output signal known as a fluorescent signal representative of the intensity of the fluorescence emission band. The output signal can then be processed by respective amplifier 60 or 62. Amplifier 60 and amplifier 62 are shown only in FIG. 1. Both amplifier 60 and amplifier 62 are optional. An amplifier is only used where it is necessary or desirable to enhance the fluorescent signal prior to its detection.

In another aspect of the instant claimed invention, illustrated in FIG. 3, rotatable mirror 24 is positioned within opening 28 of sample holder 30 such that rotatable mirror 24 is capable of rotating to move and project converging cone of excitation light 32a, converging cone of excitation light 32b or converging cone of excitation light 32c to each of Sample One 38, Sample Two 41 and Sample Three 43, respectively, as illustrated in FIG. 3. Rotatable mirror 24 can include a variety of different mirror sizes, dimensions and types. Preferably, rotatable mirror 24 includes an off-axis paraboloidal mirror. This type of mirror projects converging cone of excitation light 32a onto sample 34 in an off-axis position relative to rotatable mirror 24, thus, maximizing the amount of converging cone of excitation light 32a projected onto the sample.

Rotatable mirror 24 can be rotated manually or automatically by any suitable mechanism. It is preferred to rotate the mirror automatically. This can provide for more precise and accurate control of the rotation. The automation of the rotating mirror can be carried out in any suitable way such as by a commercially available stepper motor mechanism. The stepper motor mechanism can be controlled by an on-board or external controller as discussed below. Rotatable mirror 24 can be made to rotate about a 360 degree axis or along an angular axis that is less than a full circle (i.e., 360 degrees). In an embodiment, the samples do not completely surround rotatable mirror 24 such that it would not have to rotate an entire 360 degrees to move and project the converging cone of excitation light 32 onto each of the samples.

As previously discussed, rotatable mirror 24 of the present invention enables one to test a number of samples without having to replace and substitute one sample for another after each test run. Rotatable mirror 24 can also facilitate minimizing the ratio of scattered light to emission or fluorescent light prior to detection of the fluorescent light. In reflectance fluorometry, scattered excitation light is especially a problem with opaque samples. Scattered excitation light is many times more intense than the reflected fluorescence emission. Thus, it is desirable to suppress the scattered light as much as possible.

The undesirable reflection of excitation light (i.e., scattered light) from the optical cell and sample can be minimized by suitably positioning the focal point of rotatable mirror 24 on the optical cell such that the majority of the reflected light is cast outside of the collection volume of the mirror. Since the desired fluorescence emission is isotropic, it can be collected at full efficiency, thus giving an increase in the ratio of emission to scatter.

In particular, this result occurs when the optical cell is a round (i.e., cylindrical) glass tube 34 as shown in FIG. 1. For such round tubes, there exists two positions (symmetrically located) on the tube where the angle between the excitation beam of light and a tangent at the tube surface is such that the collected scattered light is minimized and collected emission light is highest.

By decreasing the amount of scattered light that is transmitted to the detector, the signal (the "signal" refers to the fluorescent signal corresponding to the detection of fluorescent light) to noise (the "noise" refers to the fluorescent signal corresponding to scattered light, for example) is maximized. This can provide for a more accurate and precise analysis of the measured fluorescent light without having to manipulate the output signal of the detector to cancel out or minimize the noise.

It should be appreciated that rotatable mirror 24 can be placed in any suitable position relative to the samples, particularly with respect to opening 28 of the sample holder 30 (see FIG. 3) provided that the mirror can suitably project the converging cone of excitation light onto each of the samples.

Sample holder 30 can include a variety of suitable configurations. As shown in FIG. 3, sample holder 30 may have a circular or carousel shape with an opening 28 through which the rotatable mirror 24 is positioned. The samples, Sample One 38, Sample Two 41 and Sample Three 43 are placed in optical cells (not shown in FIG. 3) which are held into position by a respective channel 36 positioned outside of opening 28. The optical cell can be any suitable shape, such as cylindrical, rectangular or the like. The optical cell is preferably cylindrically shaped as previously discussed.

It should be appreciated that the optical cell can be constructed as a flow cell (not shown) for use in on-line testing. The flow cell can be constructed and used in any suitable fashion. The preferred configuration is one that includes a flow cell with a ball which will not allow fluid to flow properly through the fluorometer if the fluorometer is inverted. However, should the fluorometer be inverted completely or tilted at any angle between 0° and 360°, it is still capable of functioning, providing a flow regulator is used that is independent of gravity. Such flow cell regulators are known in the art.

With a flow cell configuration, the fluorometer may be used to detect or test a number of samples derived from one or more process streams of a system including an industrial water system or the like. The samples can also be taken at various points along the process stream. The fluorometer can be adapted to communicate with a controller for monitoring and optionally controlling a process or system, such as an industrial or natural water system, particularly when the fluorometer is configured for on-line testing.

It should also be appreciated that the fluorometer can be adapted to agitate, heat, cool, aerate or perform other useful unit operations upon the samples during testing if the application necessitates such unit operations be applied to the samples.

FIG. 3 illustrates the configuration of the fluorometer when it is used for measuring multiple samples. In FIG. 3 rotatable mirror 24 first directs the converging cone of excitation light 32a to Sample One 38 which emits fluorescent light 40 in a diverging fan of emitted light. The fluorescent light 40 is subsequently collected by the rotatable mirror 24 and then transmitted to one or more detectors as discussed in detail previously. After Sample One 38 has been tested, rotatable mirror 24 rotates to move and projects the converging cone of excitation light 32b onto Sample Two 41 which in turn emits fluorescent light 42 in a diverging fan of emitted light. After Sample Two 41 has been tested, rotatable mirror 24 rotates to move and project the converging cone of excitation light 32c onto Sample Three 43 which in turn emits fluorescent light 44 in a diverging fan of emitted light. Rotatable mirror 24 can be rotated in any suitable sequence and direction along its rotating axis in order to analyze a portion of or all of the samples.

It should be appreciated that sample holder 30 can be constructed to hold any suitable number of samples. Preferably, the sample holder is configured to hold sixteen or fewer samples. Limitations on the number of samples include practical considerations such as costs due to, for example, the size of the mirror, sample holder, optical cells or the like. It should be appreciated that a mirror having a longer focal length may be required as the number of samples increases. However, the size of the optical cells may also be decreased to allow for an increasing number of samples to be analyzed such that the samples can be positioned within the focal length of the rotating mirror.

As previously discussed, rotatable mirror 24 collects the fluorescent light emitted by the samples. It then can transmit the emitted light to one or more detectors in a variety of different ways. As illustrated in FIGS. 1, 2 and 3, rotatable mirror 24 transmits the fluorescent light through a series of lenses and filters before it reaches the detectors. The lenses are used to adjust the size of the beam of light reflected from the sample. The reflected light can include undesirable light, such as scattered light, in addition to the fluorescence emission. The filters can be used to filter out or exclude all or at least a portion of the undesirable reflected light such that the fluorescent signal from each fluorophore is more accurately and precisely detected as previously discussed.

As shown in FIGS. 1–3, rotatable mirror 24 transmits the reflected light to the directional mirror 26 which directs it to an emission dichroic filter 46 via the piano convex lens 22, double concave lens 20 and the excitation dichroic filter 14. The emission dichroic filter 46 is used to separate the fluorescence emission into two selected fluorescence emission bands for detection. Each emission band is passed through a separate emission filter 48 or 50 and plano convex lens 52 or 54 prior to detection by a detector 56 or 58. Each of detector 56 or 58 generates an output or fluorescent signal representative of the intensity of the fluorescence emission band. The output signal can then be processed by a respective amplifier 60 or 62. Both of amplifier 60 and amplifier 62 are optional to be included in this fluorometer. An amplifier is only used where it is necessary or desirable to enhance the fluorescent signal prior to its detection. The ability to detect two different fluorescence emission bands is desirable for a variety of different applications. For example, the fluorometer can be used to detect the fluorescent signals of fluorophores in a variety of industrial processes and systems. One application of this fluorometer is to monitor the microbiological activity of an industrial process or system, such as a paper manufacturing process, an industrial water system or the like.

The present invention is not limited to detecting two emission bands from a single sample. For example, a simpler design can be used to detect a single wavelength emission from a single wavelength excitation derived from a monochromatic excitation light source, such as a light emitting diode (LED), laser or the like. The construction of a fluorometer to detect a single wavelength emission is essentially similar to that of a fluorometer that can detect two fluorescence emission bands except that the single wavelength detection fluorometer does not include the second dichroic filter (i.e., emission dichroic filter) which is used to separate the reflected light into two emission bands at right angles to one another.

The present invention can also be designed as a multiwavelength scanning reflectance fluorometer. In this configuration, the fluorometer is capable of detecting fluorescence emission over a spectral range. This enables the fluorometer to detect and/or monitor the presence of one or more fluorophores which absorb and emit different excitation and emission bands of light.

In an embodiment, a polychromatic excitation light source, such as a xenon lamp, is used to generate a spectral range of excitation light which can be transmitted or scanned through a monochromator or grating prior to reaching the rotating mirror. The collected light (i.e., reflected light from the sample which is collected by the rotating mirror) may be similarly processed by a monochromator to separate out the desired fluorescence emission. The collected light could alternatively be focused onto a fiber optic and then fed to a fiber optic-based spectrometer or monochromator. In other words, both the excitation light and emission light can be scanned to enable the fluorometer to detect fluorescence emission spectra derived from a number of different fluorophores which may be present in each sample.

It should be appreciated that the mirrors, lenses, filters, detectors, amplifiers, and excitation light sources can include a variety of different and suitable commercially available or known products. For example, the flat mirror (Part No. 01MFG013/23), the off-axis paraboloidal mirror (Part No. 02P0A013), the large plano convex mirror (Part No. 01LPX129), the double concave lens (Part No. 01LDK007), the aspheric lens (Part No. 01LAG111) and the piano convex lens (Part No. 01LPX061) are commercially available from Melles Griot, 1770 Kettering Street, Irvine, Calif. 92614 (714) 261-5600; the excitation filter (Part No. 535DF35), the excitation dichroic filter (Part No. 560DRLP), the emission dichroic filter (Part No. 630DRLP), the emission filter (Part No. 580DF35) and the emission filter (Part No. 635DF55) are commercially available from Omega Optical, P.O. Box 573, Brattleboro, Vt. 05302 (802) 254-2690; the Amplifier (Part No. Burr-Brown AFC2101) is a commercially available Dual Current Integrator from Burr-Brown, 6730 S. Tucson Blvd., Tucson, Ariz. 85706 (520) 746-1111; and the detectors, such as photodiodes (S2386-5K), are commercially available from Hamamatsu, 360 Foothill Road, Bridgewater, N.J. 08807 (908) 231-0960.

The present invention can include a variety of different and additional components for optimizing process control, monitoring and automation. In the second aspect of the instant claimed invention, the fluorometer includes a printed circuit board assembly connected to a controller, each of a suitable and known construction (not shown). For example, a commercially available controller suitable for use in the second aspect of this invention is available from Tecnova, 1486 St. Paul Ave., Gurnee, Ill. 60031 (847) 662-6260.

The printed circuit board (PCB) assemblies useful in the fluorometer of the second aspect of this invention must be fabricated to allow powering by the controller or other device of the components of the fluorometer, which include, for example, motors for the rotating mirror, drivers for the excitation sources and amplifiers to perform current-to-voltage conversion and signal amplification from the photodetectors. Circuitry to manipulate the signals and communicate the magnitude of the signals is also integral to the PCB. Additional circuitry to measure the temperature and/or the status of the flowswitch may be included.

The fluorometer can be further connected to the controller by a communication cable that enables the controller to electronically communicate with fluorometer to control the components of the fluorometer as previously discussed. A suitable communication protocol must be selected in order to operate the fluorometer. Suitable standard communication protocols include, but are not limited to, RS-232, I²C, CAN, TCP/IP and a standard RS-485 serial communication protocol. The preferred communication protocol is a standard RS-485 serial communication protocol. It is also possible to use a wireless communication protocol between the fluorometer and controller. One such suitable wireless communication protocol is Bluetooth.

The controller can include isolated, multiple analog inputs. These inputs provide information based on their signal magnitude via 4–20 mA connections. The signals are read by the analog inputs for controlling logic of the controller to provide additional levels of control to, for example, an industrial water system. In a preferred embodiment, the controller has twenty (20) discrete analog inputs.

As stated in the preceding paragraph, the controller has the capability of processing signals available over a 4–20 mA communication line. These signals can be derived from the fluorometer in addition to other analytical devices. Therefore, the controller is capable of processing signals from analytical devices that measure system factors including, but not limited to:

pH;
conductivity;
oxidation-reduction potential or "ORP";
chemical monitors for species such as calcium, magnesium, total hardness, iron, copper, chloride, sulfate, manganese, aluminum, silica, alkalinity and ammonia;
additional chemical monitors of treatment actives such as dispersant polymer, zinc, molybdate, phosphate, condensed inorganic phosphates, phosphonates and triazoles;
turbidity;
total suspended solids;
process leaks;
free residual and total oxidant/halogen/chlorine;
water temperatures;
process-side temperatures at various places in the system;
fluid flow rates on the water-side and/or process-side;
fluid velocities;
fluid pressures and differential pressures on the water-side and/or process-side;
chemical inventories/usage;
chemical pumping rates;
blowdown rates;
makeup water rates;
corrosion monitors;
fouling/deposit monitors.;
microbiological indicators; and
light absorbance of substances in water.

In addition to the analog inputs, the controller has a sufficient number of analog outputs such that it can control other equipment, besides the fluorometer. Thus, the controller is capable of operating an entire process or system, such as an industrial water system, paper mill process or the like.

It should be appreciated that a variety of different and number of controllers can be used to facilitate process automation, control and monitoring of a system that uses the fluorometer or a number of the fluorometers of the present invention. For example, a secondary controller can optionally be used to control the rate of additive chemical added to, for example, a process water of an industrial water system that is monitored by the fluorometer of the present invention. The secondary controller, if used, may be linked to the controller as well. Preferably, the secondary controller would be controlling an inert TRASAR® system, with said inert TRASAR® system being commercially available from Nalco.

As previously discussed, the fluorometer of the present invention can be used to monitor and detect the presence of one or more fluorophores in a sample removed from any suitable process or system including natural water systems, industrial water systems, paper mill processes or other like sources. The sample can include opaque light scattering materials, such as a suspensions or slurries including, for example, raw materials or coating samples of a paper mill process.

Industrial water systems include, but are not limited to, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

Opaque media suitable for analysis by the instant claimed fluorometer include specific slurries and colloids and Metal Working Fluids capable of being tested by the method of the instant claimed invention, such as, but not limited to, those used in the mineral processing industry, those used in the pulp and paper industry, those used in the ceramics industry, those used in the coatings industry and any other opaque slurry or opaque colloid or opaque Metal Working Fluid used in a natural or in an industrial process.

An operator would necessarily expend less time, effort and handling of the samples in testing a series of samples using the fluorometer of the present invention as compared to a one-channel-sample fluorometer (i.e., a fluorometer that requires the sample, after it has been tested, to be physically removed and replaced by a next sample before the next sample can be tested). In this regard, the fluorometer of the present invention is well suited for testing fragile or mixing-sensitive materials, such as thin films or layered suspensions. Further, the ease of operation of the fluorometer of the present invention for testing multiple samples makes it desirable and/or suitable for field use applications.

The fluorometer of the present invention can include a variety of different components fashioned in any acceptable configuration. It can be configured in a number of custom configurations to suit a particular application including, for example, the number of samples analyzed, the range of excitation and emission wavelengths, the rate of data collection, one-dimensional scanning of sample surfaces, optimization of fluorescence to scattering-intensity ratios and the like.

The fluorometer of the present invention can be used in a variety of different industrial water system applications as disclosed, for example, in the following U.S. patent applications. The instant claimed fluorometer and controller are capable of functioning to control a cooling water system, as described and claimed in U.S. patent application Ser. No. 09/562,397, entitled USE OF CONTROL MATRIX FOR COOLING WATER SYSTEMS CONTROL, filed May 1, 2000, now U.S. Pat. No. 6,315,909, which is herein incorporated by reference in its entirety.

The instant claimed fluorometer and controller are capable of functioning to control a boiler, as described an claimed in U.S. patent application Ser. No. 09/563,085, entitled USE OF CONTROL MATRIX FOR BOILER CONTROL, filed May 1, 2000, now U.S. Pat. No. 6,336, 058, and U.S. patent application Ser. No. 09/737,257, also entitled USE OF CONTROL MATRIX FOR BOILER CONTROL, filed Dec. 13, 2000, now U.S. Pat. No. 6,587, 753. which are both herein incorporated by reference in their entirety.

In addition to the above described method, the fluorometer of the instant claimed invention is capable of being used in conducting the method described and claimed in U.S. patent application, MEASUREMENT AND CONTROL OF SESSILE AND PLANKTONIC MIC OBIOLOGICAL ACTIVITY IN INDUSTRIAL WATER SYSTEMS, U.S. patent application Ser. No. 09/475,585, filed Dec. 30, 1999, now U.S. Pat. No. 6,329,165 and herein incorporated by reference in its entirety. When using the instant claimed fluorometer to conduct the method described and claimed in U.S. Pat. No. 6,329,165, it will be necessary to configure it so that the fluorescent signal of the unreacted fluorogenic dye and the reacted fluorogenic dye can both be measured and used to calculate the requisite ratio.

The fluorometer of the present invention can be used to monitor and optionally control the microbiological activity of an opaque medium such as an opaque slurry or opaque colloid or certain opaque Metal Working Fluids.

Certain opaque mediums include process streams derived from a process stream of a paper mill. For example, the fluorometer can be used to detect the microbiological activity of raw materials or coating samples of a paper mill process. This can be used to determine whether the raw material or coating samples exhibit a level of microbiological activity such that they cannot be used in the process or that treatment is required prior to use.

In an embodiment, a Fluorogenic Dye can be used to facilitate the monitoring of microbiological activity. The Fluorogenic Dye can include a number of components, such as resazurin and resorufin, that can be fluorometrically measured to monitor the activity as previously discussed.

The instant claimed fluorometer can be used in the method described and claimed in U.S. Pat. No. 6,440,689, entitled, "FLUORESCENT MEASUREMENT OF MICROBIOLOGICAL ACTIVITY IN AN OPAQUE MEDIUM, which is incorporated by reference in its entirety.

The following example is presented to be illustrative of the present invention and to teach one of ordinary skill how to make and use the invention. This example is not intended to limit the invention or its protection in any way.

EXAMPLE

A laboratory test was conducted to demonstrate that the fluorometer of the present invention can be used to monitor microbiological activity, particularly as it relates to microbiological activity of raw materials or coating samples of a paper mill process. To simulate such process, nine samples of an opaque medium were prepared to simulate the opaque light scattering nature of the raw materials or coating samples of the paper mill process. Each sample was ten milliliters ("ml") in size and placed within a cylindrical glass tube. To each sample, 25 ppm of a Fluorogenic Dye was added. The Fluorogenic Dye contained varying known amounts of resazurin and resorufin in each sample to simulate various levels of microbial activity as described in as described and claimed in the previously incorporated by reference U.S. patent application entitled, "FLUORESCENT MEASUREMENT OF MICROBIOLOGICAL ACTIVITY IN A SLURRY OR COLLOID. The data are included below in Table 1.

Once prepared, each sample was placed in a mirror fluorometer to detect the presence of the dye components. The fluorometer used was constructed like the fluorometer depicted in FIGS. 1 and 2. This type of configuration was desirable for detecting the presence of both the resazurin and resorufin in a single sample. Both resazurin and resorufin are excited by a collimated beam of excitation light of approximately 525 nm. Resazurin and resorufin emit fluorescent light at different emission bands. In particular, a light-emitting diode with emission centered at 525 nm with a current of 20 mA was used. In addition, a dichroic emission filter was used to selected to separate the resazurin fluorescence emission at 635 nm and the resorufin fluoresence emmission at 580 nm. The intensity of each fluorescent signal emission was detected and measured by a separate detector.

As indicated below in Table 1, the intensity ratio, i.e., the ratio of the intensity of resorufin emission ("$I_{580}$") (aka "Reacted Fluorogenic Dye" from Attorney Docket No. 5689) to the intensity of the resazurin emission ("$I_{635}$") ("Fluorogenic Dye" from Attorney Docket No. 5689) increased as the amount of resorufin in the dye increased:

TABLE 1

| Resorufin (wt %) | Calculated Intensity RATIO ($I_{580}/I_{635}$) |
| --- | --- |
| 0 | 0.3677 |
| 10 | 1.416 |
| 20 | 1.665 |
| 30 | 1.798 |
| 40 | 1.886 |
| 50 | 1.958 |
| 60 | 2.076 |
| 80 | 2.253 |
| 100 | 2.493 |

The above results of Table 1 demonstrate that there exists a correlation between a change in the intensity radio with respect to a change in the concentration of resorufin. Thus, by measuring the fluorescent emissions of resorufin and resazurin, the amount of biological activity can be quantified.

As previously discussed, the amount of resorufin increases as the amount of microbiological activity increases due to the fact that resazurin reduces to resorufin in the presence of microbiological organisms. Thus, an increase in the intensity ratio indicates the presence of more resorufin and thus the presence of increased biological activity. Based on these results, the fluorometer of the present invention can be used to detect or monitor microbiological activity of one or more samples.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A fluorometer comprising:
    an excitation light source for generating a collimated beam of excitation light;
    a rotatable mirror positioned such that it is capable of accepting a collimated beam of light from said excitation light source and projecting a converging cone of excitation light onto one or more samples;
    a sample holder comprising one or more channels, wherein each channel is capable of holding an optical cell containing a sample; and
    a detector capable of detecting the fluorescent signals from fluorophores present in said one or more samples.

2. The fluorometer of claim 1 wherein the minor is capable of rotating about a 360 degree axis.

3. The fluorometer of claim 1 wherein the mirror is an off-axis paraboloidal mirror.

4. The fluorometer of claim 1 wherein the sample holder has an opening through which the mirror is positioned to project the collimated beam of excitation light onto the optical cell.

5. The fluorometer of claim 4 wherein the optical cell comprises a cylindrical glass tube.

6. The fluorometer of claim 4 wherein the optical cell comprises a flow cell for on-line testing.

7. The fluorometer of claim 1 further comprising a directional mirror positioned to direct the collimated beam of excitation light onto the rotatable mirror positioned such that it is as e minor rotates.

8. The fluorometer of claim 1 wherein the excitation light source includes a monochromatic light source or a polychromatic light source.

9. The fluorometer of claim 1 wherein the sample is derived from raw materials or coating samples of a paper mill process.

10. The fluorometer of claim 1 wherein the optical cell comprises a flow cell for on-line monitoring and control.

11. A fluorometer system comprising:
    (a) a fluorometer comprising
        (i) an excitation light source for generating a collimated beam of excitation light;
        (ii) a rotatable mirror positioned such that it is capable of accepting a collimated beam of light from said excitation light source and projecting a converging cone of excitation light onto one or more samples;
        (iii) a sample holder comprising one or more channels, wherein each channel is capable of accepting an optical cell containing a sample;
        (iv) a detector capable of detecting the fluorescent signals from fluorophores present in said one or more samples; and
    (b) controller that uses the fluorescent signals detected by said fluorometer for monitoring of and controlling of the natural or industrial process from which the samples are taken.

12. The fluorometer system of claim 11 wherein the controller comprises one or more isolated analog inputs and outputs such that the controller is capable of using the fluorescent signal and the other analog inputs to monitor and control an industrial water system.

13. The fluorometer system of claim 12 wherein the controller processes the fluorescent signal for monitoring and controlling microbiological activity of raw materials or coating samples derived from a paper mill process.

14. A method of fluorometrically detecting fluorophores present in one or more samples, the method comprising the steps of:
    a) providing fluorometer system, wherein said fluorometer system comprises
        (i) a flurometer comprising
            an excitation light source for generating a collimated beam of excitation light;
            a rotatable mirror positioned such that it is capable of accepting a collimated beam of light from said excitation light source and projecting a converging beam of excitation light onto one or more samples;
            a sample holder comprising one or more channels, wherein each channel is
                capable of accepting an optical cell containing a sample;
            a detector capable of detecting the fluorescent signals from fluorophores present
                in said one or more samples; and
        (ii) a controller that uses the fluorescent signals detected by said fluorometer;
    b) providing one or more samples from a natural or industrial process stream;
    c) using said fluorometer to detect the fluorescent signals of said fluorophores in said samples; and
    d) operating said controller in such a way that the fluorescent signals detected by said fluorometer are used by the controller to monitor and control the natural or industrial process from which the samples are taken.

15. The method of claim 14 wherein the detected fluorescent signals are of fluorophores present in samples of raw materials or coating samples from a paper mill process.

\* \* \* \* \*